United States Patent [19]
Christensen, IV et al.

[11] Patent Number: 5,420,154
[45] Date of Patent: May 30, 1995

[54] TNF INHIBITORS

[75] Inventors: Siegfried B. Christensen, IV, Philadelphia; Klaus M. Esser, Downingtown, both of Pa.; Philip L. Simon, Randolph, N.J.

[73] Assignee: SmithKline Beecham Corp., Philadelphia, Pa.

[21] Appl. No.: 852,180

[22] PCT Filed: Jul. 29, 1991

[86] PCT No.: PCT/US91/05350
  § 371 Date: Mar. 30, 1992
  § 102(e) Date: Mar. 30, 1992

[87] PCT Pub. No.: WO90/15534
  PCT Pub. Date: Dec. 27, 1990

Related U.S. Application Data

[63] Continuation-in-part of Ser. No. 562,761, Aug. 3, 1990, abandoned.

[51] Int. Cl.$^6$ .............................................. A61K 31/40
[52] U.S. Cl. ..................................... 514/424; 548/551
[58] Field of Search ........................................ 514/424

[56] References Cited

U.S. PATENT DOCUMENTS

| | | | |
|---|---|---|---|
| 3,923,833 | 12/1975 | Gruenman et al. | 548/322 |
| 4,012,495 | 3/1977 | Schmiechen et al. | 424/274 |
| 4,034,087 | 7/1977 | Voorhees | 424/240 |
| 4,153,713 | 5/1979 | Huth et al. | 424/274 |
| 4,186,129 | 1/1980 | Huth et al. | 548/326 |
| 4,193,926 | 3/1980 | Schmiechen et al. | 260/326.5 |

FOREIGN PATENT DOCUMENTS

| | | |
|---|---|---|
| 0411754A3 | 2/1991 | European Pat. Off. . |
| 0411754A2 | 2/1991 | European Pat. Off. . |
| 3438839 | 4/1988 | Germany . |
| WO87/06576 | 11/1987 | WIPO . |
| WO90/15534 | 12/1990 | WIPO . |
| 91/65350 | 12/1991 | WIPO . |

OTHER PUBLICATIONS

Lee et al., Int. J. Immunotherapy, VA(1) pp. 1 to 12 (1990).
Peachell et al., FASEB J., vol. 4, p. A639, Abstract #2163 (1990).
Internat'l Conference, 5th Dec. 1988, Royal Lancaster Hotel, London, "Xanthines".
Frohlich et al., Abstract, J. Invest. Dermatology 90:240 (1988).
Marivet et al., J. Med. Chem., 32, pp. 1450–1457 (1989).
Torphy, New Drugs for Asthma, P. J. Barnes Ed., IBC Technical Services, Ltd., London 1989, Chapter 7, pp. 66–77.
Renz et al., J. Immunol., Release of Tumor Necrosis Factor-αFrom Macrophages, vol. 141(7), 2388–2393 (1988).

*Primary Examiner*—David B. Springer
*Attorney, Agent, or Firm*—Dara L. Dinner; Stephen Venetianer; Edward T. Lentz

[57] ABSTRACT

Derivatives of 2-pyrrolidinones are described which inhibit the production of TNF and are useful in the treatment of disease states mediated or exacerbated by TNF production.

8 Claims, No Drawings

TNF INHIBITORS

This application is a PCT 371 of PCT U.S. 91/05350 filed July 29, 1991 which is a CIP of 07/562761, filed Aug. 3, 1990, now abandoned.

FIELD OF INVENTION

The present invention relates to 4-(substituted phenyl) pyrrolidinone derivatives which inhibit the production of Tumor Necrosis Factor (TNF).

BACKGROUND OF THE INVENTION

TNF, a serum glycoprotein, has been implicated in mediating or exacerbating various mammalian conditions such as rheumatoid arthritis, rheumatoid spondylitis, osteoarthritis, gouty arthritis and other arthritic conditions; sepsis, septic shook, endotoxic shock, gram negative sepsis, toxic shook syndrome, adult respiratory distress syndrome, cerebral malaria, chronic pulmonary inflammatory disease, silicosis, pulmonary sarcoisosis, bone resorption diseases, reperfusion injury, graft vs. host reaction, allograft rejections, fever and myalgias due to infection, such as influenza, cachexia secondary to infection or malignancy, cachexia, secondary to acquired immune deficiency syndrome (AIDS), AIDS, ARC (AIDS related complex), keloid formation, scar tissue formation, Crohn's disease, ulcerative colitis, or pyresis.

AIDS results from the infection of T lymphocytes with Human Immunodeficiency Virus (HIV). At least three types or strains of HIV have been identified, i.e., HIV-1, HIV-2 and HIV-3. As a consequence of HIV infection, T-cell mediated immunity is impaired and infected individuals manifest severe opportunistic infections and/or unusual neoplasms. HIV entry into the T lymphocyte requires T lymphocyte activation. Other viruses, such as HIV-1, HIV-2 infect T lymphocytes after T Cell activation and such virus protein expression and/or replication is mediated or maintained by such T cell activation. Once an activated T lymphocyte is infected with HIV, the T lymphocyte must continue to be maintained in an activated state to permit HIV gene expression and/or HIV replication. Monokines, specifically TNF, are implicated in activated T-cell mediated HIV protein expression and/or virus replication by playing a role in maintaining T lymphocyte activation. Therefore, interference with monokine activity such as by inhibition of monokine production, notably TNF, in an HIV-infected individual aids in limiting the maintenance of T cell activation, thereby reducing the progression of HIV infectivity to previously uninfected cells which results in a slowing or elimination of the progression of immune dysfunction caused by HIV infection. Monocytes, macrophages, and related cells, such as kupffer and glial cells, have also been implicated in maintenance of the HIV infection. These cells, like T-cells, are targets for viral replication and the level of vital replication is dependent upon the activation state of the cells. [See Rosenberg et al., The Immunopathogenesis of HIV Infection, Advances in Immunology, Vol. 57, (1989)]. Monokines, such as TNF, have been shown to activate HIV replication in monocytes and/or macrophages [See Poli, et al., Proc. Nat. Acad. Sci., 87:782–784 (1990)], therefore, inhibition of monokine production or activity aids in limiting HIV progression as stated above for T-cells.

TNF has also been implicated in various roles with other viral infections, such as the cytomegalia virus (CMV), influenza virus, and herpes viruses for similar reasons as those noted.

The ability to control the adverse effects of TNF is furthered by the use of the compounds which inhibit TNF in animals who are in need of such use. There remains a need for compounds which are useful in treating TNF mediated disease states which are exacerbated or caused by the excessive and/or unregulated production of TNF.

SUMMARY OF THE INVENTION

This invention relates to a method of inhibiting TNF production in an animal, including humans, which method comprises administering to an animal in need of such treatment, an effective TNF inhibiting mount of a compound of Formula (I).

This invention also relates to a method of treating a human afflicted with a human immunodeficiency virus (HIV), which comprises administering to such human an effective TNF inhibiting mount of a compound of Formula (I).

This invention also relates to a pharmaceutical composition which comprises a compound of Formula (I) and a pharmaceutically acceptable carrier or diluent for use in the treatment of a TNF mediated disease.

The compounds of this invention useful in treating a TNF mediated disease by inhibition or reduction of the in vivo levels of TNF are represented by the structure:

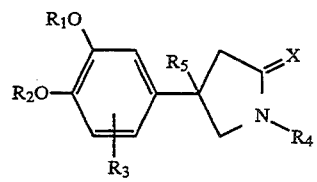

FORMULA (I)

wherein:

$R_1$ is selected from $C_{1-6}$ alkyl, $C_{2-6}$ alkenyl, $C_{3-7}$ alkynyl, $C_{3-7}$ cycloalkyl, $C_{3-7}$ cycloalkyl$C_{1-2}$alkyl, aryl, aralkyl$_{1-6}$ or a heterocyclic ring, all optionally substituted by one or more halogen atoms or by one substituent group selected from hydroxy, carboxy, $C_{1-5}$ alkoxy, $C_{1-5}$ alkoxy-carbonyl, carboxamido, $C_{1-5}$ alkylcarboxamido, $C_{1-5}$ dialkyl-carboxamido, carboxy$C_{4-7}$cyclicamido, amino, $C_{1-5}$ alkylamino, $C_{1-5}$ alkyl, $C_{2-5}$ alkylene-imino, a morpholino or piperzino ring; or $R_1$ or $R_2$ together form an alkylene chain of 1–3 carbon atoms;

$R_2$ is selected from $C_{1-4}$ alkyl, $C_{2-4}$ alkenyl, $C_{2-4}$ alkynyl all optionally substituted by one or more halogen atoms;

$R_3$ is a hydrogen atom or methoxy;

$R_4$ is a hydrogen atom, $C_{1-5}$ alkyl, aryl, aryl optionally substituted by one or two methyl groups, aralkyl, $C_{1-6}$ alkanoyl or $COR_6$;

$R_6$ is alkyl$_{1-10}$, hydroxy, O-$C_{1-10}$alkyl, aryl, aralkyl, O-aryl, O-aralkyl$_{1-10}$, $NH_2$, NH-$C_{1-10}$alkyl, NH-aryl, $N(C_{1-10}alkyl)_2$, $N(aryl)_2$, or -N(aryl)-($C_{1-10}$alkyl);

X is an oxygen or sulfur atom;

$R_5$ is hydrogen or $C_{1-4}$ alkyl; and the pharmaceutically acceptable salts thereof.

DETAILED DESCRIPTION OF THE INVENTION

This invention relates to a method of inhibiting TNF production in an animal, which method comprises administering to an animal in need of such treatment, an effective TNF inhibiting amount of a compound of Formula (I). This method may be used for the prophylactic treatment or prevention of certain TNF mediated disease states amenable thereto.

The compounds of Formula (I) are also useful in the treatment of additional viral infections, where such viruses are sensitive to upregulation by TNF or will elicit TNF production in vivo. The viruses contemplated for treatment herein are those which are sensitive to inhibition, such as by decreased replication, directly or indirectly, by the TNF inhibitors of Formula (I). Such viruses include, but are not limited to; HIV-1, HIV-2 and HIV-3 as noted above, Epstein Barr (EB) Virus, Human Papilloma Virus, Influenza, Vital Encelphalitis, Respiratory Syncytial virus (RSV), Hepatitis A, Hepatitis B, Hepatitis non A non B, and the Herpes family viruses, including, Cytomegalovirus (CMV), Herpes Varicella Zoster, and Herpes Simplex I & II.

Preferred compounds of Formula (I) of the present invention are those wherein

X is oxygen;

$R_1$ is selected from $C_{1-6}$alkyl, $C_{3-7}$ cycloalkyl, or $C_{3-7}$ cycloalkyl-$C_{1-4}$ alkyl;

$R_2$ is selected from methyl;

$R_4$ is hydrogen, $C_{1-6}$ alkanoyl, or $COR_6$;

$R_3$ is hydrogen; and $R_5$ is hydrogen.

More preferred compounds of Formula (I) are those wherein $R_1$ is $C_{3-7}$ cycloalkyl or $C_{1-6}$ alkyl and $R_4$ is hydrogen or $C_{1-6}$ alkanoyl. A more preferred embodiment is where $R_1$ is cyclopentyl or methyl. Most preferred is $R_1$ as cyclopentyl and $R_2$ as methyl. Preferable halo substituent groups are fluorine and chlorine.

Specifically exemplified is 4-[3-(cyclopentyloxy)-4-methoxyphenyl]-2-pyrrolidinone.

By the term "$C_{1-6}$alkyl" or "alkyl" groups as used herein is meant to include both straight or branched chain radicals of 1 to 7 carbon atoms, unless the chain length is limited thereto, including, but not limited to methyl, ethyl, n-propyl, isopropyl, n-butyl, sec-butyl, isobutyl, tert-butyl, and the like.

By the term "alkenyl" as used herein is meant to include, but not limited to vinyl, 1-propenyl, 2-propenyl, 2-propinyl or 3-methyl-2-propenyl.

By the term "cycloalkyl" or "cycloalkyl alkyl" as used herein is meant to include groups of 3-7 carbon atoms, such as cyclopropyl, cyclopropylmethyl, cyclopentyl or cyclohexyl.

By the term "aryl" or "aralkyl" as used herein is meant an aromatic ring or ring system of 6-10 carbon atoms, preferably monocycle, such as phenyl, benzyl, phenethyl or naphthyl.

By the term "heterocyclic ring" as used herein is meant a saturated ring of 5 to 6 members having a single oxygen, sulfur or nitrogen atom, such as, but not limited to 2- and 3-tetrahydropyranyl, 2- and 3-tetrahydrofuranyl, pyrrolidino, 2- and 3-pyrrolidyl, piperidinino, 2-, 3- and 4-piperidyl and the corresponding N-alkyl pyrrolidyl and piperidyl rings wherein the alkyl is of 1 –4 carbon atoms. Also encompassed within the scope of this invention are heterocyclic rings having more than one hetero atom such as morpholino, piperazino or N-alkyl piperazino.

By the term "halo" as used herein is meant all halogens, i.e., chloro, fluoro, bromo and iodo.

By the term "inhibiting the production of IL-1" or "inhibiting the production of TNF" is meant a) a decrease of excessive in vivo IL-1 or TNF levels, respectively, in a human to normal levels or below normal levels by inhibition of the in vivo release of IL-1 by all cells, including but not limited to monocytes or macrophages;

b) a down regulation, at the translational or transcription level, of excessive in vivo IL-1 or TNF levels, respectively, in a human to normal levels or below normal levels; or c) a down regulation, by inhibition of the direct synthesis of IL-1 or TNF levels as a postranslational event.

By the term "TNF mediated disease or disease states" is meant any and all disease states in which TNF plays a role, either by production of TNF itself, or by TNF causing another cytokine to be released, such as but not limited to IL-1, or IL-6. A disease state in which IL-1, for instance, is a major component, and whose production or action, is exacerbated or secreted in response to TNF, would therefore be considered a disease state mediated by TNF. As TNF-$\beta$ (also known as lymphotoxin) has close structural homology with TNF-$\alpha$ (also known as cachectin) and since each induces similar biologic responses and binds to the same cellular receptor, both TNF-$\alpha$ and TNF-$\beta$ are inhibited by the compounds of the present invention and thus are herein referred to collectively as "TNF" unless specifically delineated otherwise. Preferably TNF-$\alpha$ is inhibited.

By the term "cytokine" as used herein is meant any secreted polypeptide that affects the functions of other cells, and is a molecule which modulates interactions between cells in the immune or inflammatory response. A cytokine includes, but is not limited to monokines and lymphokines regardless of which cells produce them. For instance, a monokine is generally referred to as being produced and secreted by a mononuclear cell, such as a macrophage and/or monocyte but many other cells produce monokines, such as natural killer cells, fibroblasts, basophils, neutraphils, endothelial cells, brain astrocytes, bone marrow stromal cells, epideral keratinocytes, and $\beta$-lymphocytes. Lymphokines are generally referred to as being produced by lymphoctye cells. Examples of cytokines for the present invention include, but are not limited to, Interleukin-1 (IL-1), Interleukin-6 (IL-6), Interleukin-8 (IL-8), Tumor Necrosis Factor-alpha (TNF$\alpha$) and Tumor Necrosis Factor beta (TNF$\beta$).

The compounds of the present invention may contain one or more asymmetric carbon atoms and may exist in racemic and optically active forms. All of these compounds are contemplated to be within the scope of the present invention.

The preparation of the compounds of Formula (I) can be carried out by one of skill in the art according to the procedures outlined in the Example section, infra, or by Schmiechen et al., U.S. Pat. No. 4,012,495, Mar. 5, 1977; Schmiechen et al., U.S. Pat. No. 4,193,926, Mar. 18, 1980; Huth et al., U.S. Pat. No. 4,153,713, May 8, 1979; Saccomano et at., WO 87/06576 Nov. 5, 1987; and in Marivet et al., J. Med Chem., Vol. 32, pages 1450–57 (1989).

The compounds of Formula (I) wherein $R_5$ is alkyl may be prepared by analagous methods to those illustrated above, notably U.S. Pat. No. 4,193,926, by using an appropriately substituted alkylphenone (substituted with the appropriate $R_5$ alkyl group) as opposed to using the benzaldehyde described in the cited patent literature. Alternatively the compounds may be prepared by the processes exemplified in Klose et al., DE 3438839.

The compounds of Formula (I) or a pharmaceutically acceptable salt thereof, can be used in the manufacture of a medicament for the treatment, prophylactically or therapeutically of any disease state in an animal which is exacerbated or caused by TNF production by such animal's cells, such as but not limited to monocytes and/or macrophages, especially caused by excessive or unregulated TNF production. The compounds of Formula (I) are administered in an mount sufficient to inhibit TNF production such that it is regulated down to normal levels, or in some case to subnormal levels, so as to meliorate the disease state. Abnormal levels of TNF, for the present invention, constitute levels of 1) free (not cell bound) TNF, greater than or equal to 1 picogram per ml; 2) any cell associated TNF; or 3) the presence of TNF mRNA above basal levels in cells or tissues in which TNF is produced.

There are several disease states in which excessive or unregulated TNF production by monocytes and/or macrophages is implicated in exacerbating and/or causing the disease. These include endotoxemia and/or toxic shock syndrome [See Tracey et al., *Nature* 330:662–664 (1987); and Hinshaw et at., *Circ. Shock* 30:279–292 (1990)]; cachexia [See, Dezube et al., *Lancet*, 335 (8690):662 (1990)]; Adult Respiratory Distress Syndrome where TNF concentration in excess of 12,000 pg/ml have been detected in pulmonary aspirates from ARDS patients. [See, Miller et al., *Lancet* 2(8665):712–714 (1989). Systemic infusion of recombinant TNF resulted in changes typically seen in ARDS [See, Ferrai-Baliviera et al., *Arch. Surg.* 124(12);1400–1405 (1989)]; AIDS where viral replication of latent HIV in T-cell and macrophage lines can be induced by TNF [See, Folks et al., *PNAS* 86:2365–2368 (1989)]. A molecular mechanism for the virus inducing activity is suggested by TNFs ability to activate a gene regulatory protein (NF-kB) found in the cytoplasm of cells, which promotes HIV replication through binding to a viral regulatory gene sequence (LTR) [See, Osborn et al., *PNAS* 86:2336–2340 (1989)]. TNF in AIDS associated cachexia is suggested by elevated serum TNF and high levels of spontaneous TNF production in peripheral blood monocytes from patients [See, Wright et at., *J. Immunol.* 141(1):99–104 (1988)]. TNF in Bone Resorption Diseases, including arthritis, wherein it has been determined that when activated, leukocytes will produce a bone-reasorbing activity, and data suggests that TNF-α and TNF-β both contribute to this activity. [See e.g., Bertolini et al., Nature 319:516–518 (1986) and Johnson et al., *Endocrinology* 124(3):1424–1427(1989)]. It has been determined that TNF stimulates bone resorption and inhibits bone formation in vitro and in vivo through stimulation of osteoclast formation and activation combined with inhibition of osteoblast function. Although TNF may be involved in many bone resorption diseases, including arthritis, the most compelling link with disease is the association between production of TNF by tumor or host tissues and malignancy associated hypercalcemia [See, *Calci. Tissue Int.* (*US*) 46(Suppl.):S3–10 (1990)]. In Graft versus Host Reaction, increased serum TNF levels have been associated with major complication following acute allogenic bone marrow transplants [See, Holler et al., *Blood,* 75(4):1011–1016(1990)]; cerebral malaria, which is a lethal hyperacute neurological syndrome associated with high blood levels of TNF and is the most severe complication occurring in malaria patients. A form of experimental cerebral malaria (ECM) that reproduces some features of the human disease was prevented in mice by administration of an anti-TNF antibody. [See, Grau et at., *Imm. Review* 112:49–70 (1989)]. Levels of serum TNF correlated directly with the severity of disease and prognosis in patients with acute malaria attacks [See Grau et al., *N. Engl. J. Med.* 320(24):1586–1591 (1989)]. Another disease state in which TNF plays a role is the area of chronic Pulmonary Inflammatory Diseases. The deposition of silica particles leads to silicosis, a disease of progressive respiratory failure caused by a fibrotic reaction. Antibody to TNF completely blocked the silica-induced lung fibrosis in mice [See Piguet et al., *Nature*, 344:245–247 (1990)]. High levels of TNF production (in the serum and in isolated macrophages) have been demonstrated in animal models of silica and asbestos induced fibrosis [See Bissonnette et al., *Inflammation* 13(3):329–339 (1989)]. Alveolar macrophages from pulmonary sarcoidosis patients have also been found to spontaneously release massive quantities of TNF as compared with macrophages from normal donors [See Baughman et al., *J. Lab. Clin. Med.* 115(1):36–42 (1990)]. TNF is also implicated in another acute disease state such as the inflammatory response which follows reperfusion, called Reperfusion Injury and is a major cause of tissue damage after loss of blood flow [See, Vedder et al., *PNAS* 87:2643–2646 (1990)]. TNF also alters the properties of endothelial cells and has various pro-coagulant activities, such as producing an increase in tissue factor pro-coagulant activity and suppression of the anticoagulant protein C pathway as well as down-regulating the expression of thrombomodulin [See, Sherry et al., *J. Cell Biol.* 107:11269–1277 (1988)]. TNF also has pro-inflammatory activities which together with its early production (during the initial stage of an inflammatory event) make it a likely mediator of tissue injury in several important disorders including but not limited to, myocardial infarction, stroke and circulatory shock. Of specific importance may be TNF-induced expression of adhesion molecules, such as intercellular adhesion molecule (ICAM) or endothelial leukocyte adhesion molecule (ELAM) on endothelial cells [See, Munro et al., *Am. J. Path.* 135(1):121–132 (1989)].

The method of treatment and monitoring for an HIV-infected human manifesting immune dysfunction or cytokine-mediated disease associated problems is taught in Hanna, WO 90/15534, Dec. 27, 1990. In general, an initial treatment regimen can be copied from that known to be effective in interfering with TNF activity for other TNF mediated disease states by the compounds of Formula (I). Treated individuals will be regularly checked for T cell numbers and T4/T8 ratios and/or measures of viremia such as levels of reverse transcriptase or viral proteins, and/or for progression of monokine-mediated disease associated problems such as cachexia or muscle degeneration. If no effect is seen following the normal treatment regimen, then the amount of the monokine activity interfering agent administered is increased, e.g., by fifty percent per week.

The compounds of Formula (I) may be used topically in the treatment or prophylaxis of topical disease states mediated or exacerbated by excessive TNF production, respectively, such as rheumatoid arthritis, rheumatoid spondylitis, osteoarthritis, gouty arthritis and other arthritic conditions, inflamed joints, eczema, psoriasis or other inflammatory skin conditions such as sunburn; inflammatory eye conditions including conjunctivitis; pyresis, pain and other conditions associated with inflammation.

Preferably the compounds of Formula (I) are useful in the treatment of TNF mediated disease states, other than or in addition to topical inflammatory diseases, such as eczema, psoriasis or other inflammatory skin conditions such as sunburn; or inflammatory eye conditions including conjunctivitis. Or more preferably the compounds of Formula (I) useful in the treatment of TNF mediated disease states, other than or in addition to generally accepted inflammatory disease states, such as rheumatoid arthritis, rheumatoid spondylitis, osteoarthritis, gouty arthritis and other arthritic conditions, etc.; and including asthma.

In addition, the present invention attributes many of the biological disease states attributable to interleukin-1 (IL-1) activity as being attributable to that of TNF activity as well. A comprehensive listing of IL-1 activities can be found in Dinarello, *J. Clinical Immunology*, 5 (5), 287–297 (1985). It should be noted that some of these effects have been described by others as indirect effects of IL- 1.

Interleukin-1 (IL- 1) has been demonstrated to mediate a variety of biological activities thought to be important in immunoregulation and other physiological conditions such as inflammation [See, e.g., Dinarello et al., *Rev. Infect. Disease*, 6, 51 (1984)]. The myriad of known biological activities of IL-1 include the activation of T helper cells, induction of fever, stimulation of prostaglandin or collagenase production, neutrophil chemotaxis, induction of acute phase proteins and the suppression of plasma iron levels. These disease states are also considered appropriate disease states of TNF activity and hence compounds of Formula (I) are also useful in their treatment as well, and the use of the compounds of Formula (I) should not be considered solely limited to the specifically described TNF mediated disease states herein. The compounds of the present invention should be efficacious in an IL-1 mediated disease state as TNF and IL-1 act in a synergistic manner. TNF as well mediates the release, in some instances, of the monokine IL-1, therefore a reduction in the levels of TNF may be useful in the treatment of a disease state wherein IL-1 is a major component.

The present invention therefore, relates to an effective, TNF production inhibiting amount of a compound of Formula (I) or a pharmaceutically acceptable salt thereof, useful in treating, prophylactically or therapeutically, any disease state in a human which is exacerbated or caused by excessive or unregulated TNF production. Also the present invention relates therefore, to an effective, TNF production inhibiting amount of a compound of Formula (I) or a pharmaceutically acceptable salt thereof is useful in treating, prophylactically or therapeutically, any disease state in a human which is exacerbated or caused by excessive or unregulated IL-1 production, i.e. where IL-1 is a major component, by such human's monocytes and/or macrophages.

The pharmaceutical composition of the present invention will comprise an effective, non-toxic amount of a compound of Formula (I) and a pharmaceutically acceptable carrier or diluent. The compounds of Formula (I) as used herein, are administered in conventional dosage forms prepared by combining a compound of Formula (I) in an effective mount sufficient to produce the desired activity, respectively, with standard pharmaceutical carriers according to conventional procedures. These procedures may involve mixing, granulating and compressing or dissolving the ingredients as appropriate to the desired preparation.

The pharmaceutical carrier employed can be readily determined by one of skill in the art who will recognize that such determination will depend upon various well-known factors such as the nature, quantity and character of the particular monokine activity interfering agent being employed and the form and route of administration desired. The carriers employed may be those described elsewhere herein.

The methods of this particular invention, for treating a viral infection, including an HIV-infected individual, may be carried out by delivering the TNF inhibiting compound of Formula (I), topically.

By topical administration herein is meant non-systemic administration and includes the application of a TNF interfering agent externally to the epidermis, to the buccal cavity and instillation of such a compound into the ear, eye and nose, and where the compound does not significantly enter the blood stream.

The pharmaceutical carrtier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl monostearate or glyceryl distearate alone or with a wax.

Compounds of Formula (I) and their pharmaceutically acceptable salts (when possible), some of which are orally active, can be employed in a wide variety of pharmaceutical forms. The preparation of a pharmaceutically acceptable salt will be determined by the nature of the compound itself, and can be prepared by conventional techniques readily available to one skilled in the art. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1 gram. When a liquid carrier is used, the preparation will be in the form of a syrup, emulsion, soft gelatin capsule, sterile injectable liquid such as an ampule or nonaqueous liquid suspension. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils and are incorporated in a soft gelatin capsule shell. A syrup formulation will generally consist of a suspension or solution of the compound or salt in a liquid carrier for example, ethanol, glycerine or water with a flavoring or coloring agent.

The amount of a compound of Formula (I) required for therapeutic effect on administration will, of course, vary with the compound chosen, the nature and severity of the condition and the animal undergoing treatment, and is ultimately at the discretion of the physician.

The term 'parenteral' as used herein includes intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques.

Typical parenteral compositions consist of a solution or suspension of the compound or salt in a sterile aqueous or non-aqueous carrier optionally containing a parenterally acceptable oil, for example polyethylene glycol, polyvinylpyrrolidone, lecithin, arachis oil, or sesame oil. The daily dosage regimen for inhibition of TNF production, via parenteral administration is suitably about 0.001 mg/Kg to 40 mg/Kg of a compound of the Formula (I) or a pharmaceutically acceptable salt thereof calculated as the free base.

The compounds of Formula (I) may be administered orally. Each dosage unit for oral administration contains suitably from 1 mg to 100 mg, and preferably from 10 mg to 30 mg of a compound of Formula (I) or a pharmaceutically acceptable salt thereof calculated as the free base.

The daily dosage regimen for oral administration is suitably about 0.001 mg/Kg to 100 mg/Kg, preferably 0.01 to 40 mg/Kg of a compound of Formula (I) or a pharmaceutically acceptable salt thereof calculated as the free base. The active ingredient may be administered from 1 to 6 times a day, sufficient to exhibit antiinflammatory activity.

The compounds of Formula (I) may also be administered by inhalation. By "inhalation" is meant intranasal and oral inhalation administration. Appropriate dosage forms for such administration, such as an aerosol formulation or a metered dose inhaler, may be prepared by conventional techniques. The daily dosage regimen for a compound of Formula (I) for intranasal administration and oral inhalation is suitably about 0.1 to about 1200 mg.

Typical compositions for inhalation are in the form of a solution, suspension or emulsion that may be administered as a dry powder or in the form of an aerosol using a conventional propellant such as dichlorodifluoromethane or trichlorofluoromethane.

Preferably the composition is in unit dosage form, for example a tablet, capsule or metered aerosol dose, so that the patient may administer to himself a single dose.

By systemic administration is meant oral, intravenous, intraperitoneal and intramuscular administration. By topical administration is meant non-systemic administration and includes the application of a compound of Formula (I) externally to the epidermis, to the buccal cavity and instillation of such a compound into the ear, eye and nose, and where the compound does not significantly enter the blood stream.

A suitable dose of a TNF production inhibiting compound of Formula (I) is 0.001 mg to about 100 mg of base for topical administration, the most preferred dosage being about 0.01 mg to about 30 mg, for example, 0.003 mg to 10 mg administered two or three times daily.

While it is possible for an active ingredient to be administered alone as the raw chemical, it is preferable to present it as a pharmaceutical formulation. The active ingredient may comprise, for topical administration, from 0.001% to 10% w/w, e.g. from 1% to 2% by weight of the formulation although it may comprise as much as 10% w/w but preferably not in excess of 5% w/w and more preferably from 0.1% to 1% w/w of the formulation.

The topical formulations of the present invention comprise an active ingredient together with one or more acceptable carrier(s) therefor and optionally any other therapeutic ingredient(s). The carrier(s) must be 'acceptable' in the sense of being compatible with the other ingredients of the formulation and not deleterious to the recipient thereof.

Formulations suitable for topical administration include liquid or semi-liquid preparations suitable for penetration through the skin to the site of inflammation such as liniments, lotions, creams, ointments or pastes, and drops suitable for administration to the eye, ear or nose.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent The resulting solution may then be clarified by filtration, transferred to a suitable container which is then sealed and sterilized by autoclaving or maintaining at 98°–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semisolid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as prolylene glycol or macrogols. The formulation may incorporate any suitable surface active agent such as an anionic, cationic or non-ionic sulfactant such as sorbitan esters or polyoxyethylene derivatives thereof. Suspending agents such as natural gums, cellulose derivatives or inorganic materials such as silicaceous silicas, and other ingredients such as lanolin, may also be included.

It will be recognized by one of skill in the art that the form and character of the pharmaceutically acceptable carrier or diluent is dictated by the amount of active ingredient, (a compound of Formula (I)) with which it is to be combined, the route of administration and other well-known variables.

It will be recognized by one of skill in the art that the optimal quantity and spacing of individual dosages of a compound of Formula (I) or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal come of treatment, i.e., the number of doses of a compound of Formula (I) or a pharmaceutically acceptable salt thereof given per day for a defined number of days, can be ascertained by those skilled in the art using conventional course of treatment determination tests.

UTILITY EXAMPLES

Example A

Inhibitory Effect of compounds of Formula (I) on in vitro TNF production by Human Monocytes The inhibitory effect of compounds of Formula (I) on in vitro TNF production by Human Monocytes can be determined by the protocol as described in Badger et al., EPO published Application 0 411 754 A2, Feb. 6, 1991, and in Hanna, WO 90/15534, Dec. 27, 1990.

Inhibition of LPS-Induced Human Monocyte TNF Production by 4-[(3-Cyclopentyloxy-4-methoxyphenyl]-2-pyrrolidinone demonstrated an IC$_{50}$(mM) of 0.15.

UTILITY EXAMPLE B

Two models of endotoxin shock have been utilized to determine in vivo TNF activity for the compounds of Formula (I). The protocol used in the models is described in in Badger et al., EPO published Application 0 411 754 A2, Feb. 6, 1991, and in Hanna, WO 90/15534, Dec. 27, 1990. These two models, the P. acnes/LPS model and LPS/GAL model, protection from the lethal effects of endotoxin shock is provided by the compound 4-[(3-Cyclopentyloxy-4-methoxyphenyl]-2-pyrrolidinone (herein called Compound) which showed reduction of the in vivo level of tumor necrosis factor (TNF).

The data shown herein demonstrate that the compounds of the present invention inhibit TNF production in a mammal. Therefore, the compounds of the present invention are useful in inhibiting the production of rumor necrosis factor (TNF) by monocytes or macrophages in a human.

SYNTHETIC EXAMPLES

Example 1

4-[(3-Cyclopentyloxy-4-methoxyphenyl]-2-pyrrolidinone a) 3-Cyclopentyloxy-4-methoxybenzaldehyde. A mixture of 3-hydroxy-4-methoxybenzaldehyde (100 grams (g hereinafter), 0.66 moles (mol hereinafter)), potassium carbonate (100 g, 0.73 mol) and bromocyclopentane (80 miliLiters (mL hereinafter), 0.79 mol) in dimethylformamide (0.5 Liters (L hereinafter)) was heated under an argon atmosphere at 100° Centigrade (C hereinafter). After 22 hours (h hereinafter), additional bromocyclopentane (10 mL, 0.1 mol) and potassium carbonate (20 g, 0.14 mol) were added and heating was continued for 24 h. The mixture was allowed to cool and was filtered. The filtrate was concentrated under reduced pressure and the residue was partitioned between ether and aqueous sodium carbonate. The organic extract was washed with aqueous sodium carbonate and dried (potassium carbonate). The solvent was removed in vacuo and the residue was purified by flash chromatography, eluting with 2:1 hexanes/ether to provide a pale yellow oil (121 g, 84%).

Analysis Calc. for $C_{13}H_{16}O_3$: C 70.89, H 7.32; found: C 70.71, H 7.33.

b) Dimethyl (3-Cyclopentyloxy-4-methoxybenzylidene)malonate. To a solution of 3-cyclopentyloxy-4-methoxybenzaldehyde (66.1 g, 0.3 mol) in toluene (100 mL) under an argon atmosphere was added piperidine (1.5 mL, 15 mmol) and acetic acid (0.85 mL, 15 mmol). The resulting mixture was heated at reflux with azeotropic removal of water for 6 h, then allowed to cool to room temperature. The solvent was removed in vacuo and the residue was partitioned between ether and saturated aqueous sodium carbonate. The organic extract was dried (potsssium carbonate) and the solvent removed in vacuo to provide an orange oil (101 g) which was used without purification.

c) Methyl-3-cyano-3-(3-cyclopentyloxy-4-methoxyphenyl)propionate. To a solution of dimethyl (3-cyclopentyloxy-4-methoxy-benzylidene)malonate (25 g, 0.075 mol) in methanol (150 mL) was added a solution of potassium cyanide (4.9 g, 0.075 mmol) in water (20 mL). The mixture was heated at 65°–70° C. under an argon atmosphere for 6 h, cooled to room temperature and carefully acidified to pH 3 with hydrochloric acid. The liquids were removed in vacuo and the residue was partitioned between ether and aqueous sodium bicarbonate. The ether layer was dried, the solvent removed in vacuo and the residue was purified by flash chromatography, eluting with 20% ethyl acetate/hexanes to provide a solid (14.6 g, 64%): m.p. 69°–71 ° C.

d) 4-[3-Cylcopentyloxy-4-methoxy-phenyl]-2-propionate To a solution of methyl 3-cyano-3-(3-cyclopentyloxy-4-methoxy-phenyl)-propionate (10.2 g, 34 mmol) in methanol (200 mL) was added 70% perchloric acid (4 mL) and 10% palladium on activated carbon (2 g). The resulting mixture was hydrogenated at 60 psi hydrogen for 1 h and filtered through a pad of Celite. The filtrate was concentrated in vacuo. The residue was partitioned between methylene chloride and aqueous sodium carbonate and the methylene chloride layer was dried (potassium carbonate). Solvent removal provided the amine as an oil (10.9 g). This oil in toluene (130 mL) containing sodium cyanide (42 mag) under an argon atmosphere was heated at gentle reflux for 17 h. The solvent was removed in vacuo and the mixture was partitioned between dilute hydrochloric acid and methylene chloride. The organic layer was dried (potassium carbonate), the solvent was removed in vacuo and the residue was recrystallized from methylene chloride/ether to provide a solid (8.4 g, 90%): m.p. 130°–131° C.

Analysis Calc. for $C_{16}H_{21}NO_3$: C 69.79, H 7.69, N 5.09; found: C 69.90, H 7.72, N 5.15.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

We claim:

1. A method of treating a TNF mediated disease in an animal, other than or in addition to asthma, or a topical inflammatory disease, which comprises administering to said animal in need thereof an effective TNF inhibiting amount of a compound according to the formula:

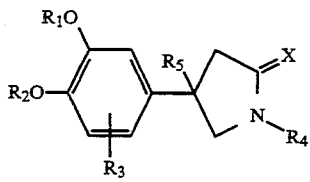

FORMULA (I)

wherein:

$R_1$ is cyclopentyl;

$R_2$ is selected from $C_{1-4}$ alkyl, $C_{2-4}$ alkenyl, $C_{2-4}$ alkynyl all optionally substituted by one or more halogen atoms;

$R_3$ is a hydrogen atom or methoxy;

$R_4$ is a hydrogen atom, $C_{1-5}$ alkyl, aryl, aryl optionally substituted by one or two methyl groups, aralkyl, $C_{1-6}$ alkanoyl or $COR_6$;

$R_6$ is alkyl$_{1-10}$, hydroxy, O-$C_{1-10}$alkyl, aryl, aralkyl, O-aryl, O-aralkyl$_{1-10}$, $NH_2$, NH-$C_{1-10}$alkyl, NH-aryl, N($C_{1-10}$alkyl)$_2$, N(aryl)$_2$, or -N(aryl)($C_{1-10}$alkyl);

X is an oxygen or sulfur atom;

$R_5$ is hydrogen or $C_{1-4}$ alkyl; and the pharmaceutically acceptable salts thereof.

2. The method according to claim 1 where the compound is 4-[3-cyclopentyloxy-4-methoxyphenyl]-2-pyrrolidinone.

3. A method of treating a human afflicted with a viral disease which comprises administering to such human an effective TNF inhibiting amount of 4-[3-cyclopentyloxy-4-methoxyphenyl]-2-pyrrolidinone or a pharmaceutically acceptable salt thereof.

4. A method of treating a human afflicted with septic shock, endotoxic shock or toxic shock syndrome which comprises administering to such human an effective TNF inhibiting amount of 4-[3-cyclopentyloxy-4-methoxyphenyl]-2-pyrrolidinone or a pharmaceutically acceptable salt thereof.

5. A method of treating a human afflicted with cerebral malaria, a herpes family virus infection or influenza viral infection which comprises administering to such human an effective TNF inhibiting amount of 4-[3-cyclopentyloxy-4-methoxyphenyl]-2-pyrrolidinone or a pharmaceutically acceptable salt thereof.

6. The method according to claim 1, wherein the animal is a human afflicted with a viral disease.

7. The method according to claim 1 wherein the animal is a human afflicted with septic shock, endotoxic shock or toxic shock syndrome.

8. The method according to claim 1 wherein the animal is a human afflicted with cerebral malaria, a herpes family virus infection or influenza viral infection.

* * * * *